United States Patent
Zenhausern (10) Patent No.: US 6,975,944 B1
(45) Date of Patent: Dec. 13, 2005

(54) METHOD AND APPARATUS FOR MONITORING MATERIALS USED IN ELECTRONICS

(75) Inventor: Frederic Zenhausern, Skillman, NJ (US)

(73) Assignee: Alpha MOS, Toulouse (FR)

( * ) Notice: Subject to any disclaimer, the term of this patent is extended or adjusted under 35 U.S.C. 154(b) by 0 days.

(21) Appl. No.: 09/407,581

(22) Filed: Sep. 28, 1999

(51) Int. Cl.[7] .............................................. G01N 27/00
(52) U.S. Cl. ............................ 702/22; 702/23; 702/24; 702/30; 702/31
(58) Field of Search ............................ 702/136, 22–24, 702/27, 28, 30–36, 40, 56, 57, 64, 65, 81–84, 702/99, 104, 113–119, 124, 126, 130, 133, 702/132, 134, 138, 183, 184, 189; 422/70, 422/89, 68.1, 88, 98, 50, 83, 90, 82.01, 82.12, 422/82.13, 82.05, 82.02, 82.03, 82.06, 61, 422/62, 67, 69, 81, 82.04, 76, 77, 82.11, 51; 436/149, 151, 806, 43, 157; 435/287.1, 287.9, 435/288.7; 204/403, 400, 401, 406–410, 204/416, 298.11

(56) References Cited

U.S. PATENT DOCUMENTS

| | | | |
|---|---|---|---|
| 5,004,914 A | | 4/1991 | Vali et al. |
| 5,015,843 A | | 5/1991 | Seitz et al. |
| 5,025,346 A | | 6/1991 | Tang et al. |
| 5,098,659 A | * | 3/1992 | Yim et al. ............... 422/82.07 |
| 5,121,337 A | | 6/1992 | Brown |
| 5,244,813 A | * | 9/1993 | Walt et al. .................. 436/172 |
| 5,349,189 A | | 9/1994 | Maggard |
| 5,363,707 A | | 11/1994 | Augenblick et al. |
| 5,406,829 A | * | 4/1995 | Ravel et al. ............... 73/24.01 |
| 5,436,167 A | | 7/1995 | Robillard |
| 5,445,008 A | | 8/1995 | Wachter et al. |
| 5,465,608 A | | 11/1995 | Lokshin et al. |
| 5,469,369 A | * | 11/1995 | Rose-Pehrsson et al. ... 364/497 |
| 5,512,490 A | * | 4/1996 | Walt et al. .................. 436/171 |
| 5,552,272 A | * | 9/1996 | Bogart ............................ 435/6 |
| 5,563,707 A | | 10/1996 | Prass et al. |
| 5,596,992 A | | 1/1997 | Haaland et al. |
| 5,641,962 A | | 6/1997 | Perry et al. |

(Continued)

FOREIGN PATENT DOCUMENTS

EP 0572335 A2 * 12/1993

(Continued)

OTHER PUBLICATIONS

Julian W. Gardner and Philip N. Bartlett, "A Brief History of Electronic Noses," Sensors and Actuators B, 18-19 (1994), 211-220.

(Continued)

*Primary Examiner*—Carol S. W. Tsai
(74) *Attorney, Agent, or Firm*—Fox Rothschild LLP; Patrick Higgins (57) ABSTRACT

A method and apparatus suitable for monitoring the quality and/or performance of a processing aid or a component during manufacture, storage, or use of electronics or electronic assemblies is provided. The apparatus incorporates a sampling device, a multivariate sensing system (e.g., a multi-sensor array or at least one sensor capable of measuring multiple variables) capable to process an analysis of low vapor pressure or vaporizable constituents in electronics by detecting some changes in the physico-chemical properties of the sensor and/or electronics and applying multivariate analysis. In one embodiment, the sensing system comprises an array of metal oxide sensors and a multivariate analysis algorithm for data processing. This method and apparatus can be employed for various quality control purposes such as contamination analysis or failure analysis of integrated circuits components.

15 Claims, 4 Drawing Sheets

U.S. PATENT DOCUMENTS

| | | | |
|---|---|---|---|
| 5,699,270 A | | 12/1997 | Ashe et al. |
| 5,732,476 A | * | 3/1998 | Pare .......................... 34/265 |
| 5,736,782 A | * | 4/1998 | Schairer ..................... 257/679 |
| 5,739,034 A | | 4/1998 | Arnvidarson et al. |
| 5,752,019 A | | 5/1998 | Rigoutsos et al. |
| 5,756,279 A | * | 5/1998 | Ebersole et al. ................ 435/4 |
| 5,788,833 A | * | 8/1998 | Lewis et al. ................. 205/787 |
| 5,801,297 A | | 9/1998 | Mifsud et al. |
| 5,807,701 A | | 9/1998 | Payne et al. |
| 5,911,872 A | * | 6/1999 | Lewis et al. ................. 205/787 |
| 5,918,289 A | | 6/1999 | Scheppers et al. |
| 5,928,880 A | * | 7/1999 | Wilding et al. ............ 435/7.21 |
| 5,976,466 A | * | 11/1999 | Ratner et al. ............ 422/82.11 |
| 6,085,576 A | * | 7/2000 | Sunshine et al. .......... 73/29.01 |
| 6,093,308 A | * | 7/2000 | Lewis et al. ................. 205/787 |
| 6,234,006 B1 | * | 5/2001 | Sunshine et al. .......... 73/29.01 |
| 6,330,464 B1 | * | 12/2001 | Colvin et al. ............... 600/316 |
| 6,387,329 B1 | * | 5/2002 | Lewis et al. .................. 422/98 |
| 6,418,783 B2 | * | 7/2002 | Sunshine et al. .......... 73/29.01 |
| 6,450,008 B1 | * | 9/2002 | Sunshine et al. .......... 73/23.34 |
| 6,467,333 B2 | * | 10/2002 | Lewis et al. ............... 73/31.05 |
| 6,658,915 B2 | * | 12/2003 | Sunshine et al. ............ 73/23.2 |
| 2002/0005580 A1 | * | 1/2002 | Goodman et al. .......... 257/734 |
| 2002/0094531 A1 | * | 7/2002 | Zenhausern .................... 435/6 |

FOREIGN PATENT DOCUMENTS

| | | | |
|---|---|---|---|
| WO | WO 95/16247 | * | 6/1995 |
| WO | WO 99/40423 | * | 8/1999 |

OTHER PUBLICATIONS

J.R. Barnes et al., "A Femtojoule Calorimeter Using Micromechanical Sensors," Rev. Sci. Instrum. 65 (12), Dec. 1994, 3793-3798.

Todd A. Dickinson, et al., "A Chemical-Detecting System Based on a Cross-reactive Optical Sensor Array," Nature, vol. 382, Aug. 22, 1996, 697-700.

H.M. Heise, A. Bittner, "Multivariate Calibration for Near-infrared Spectorscopic Assays of Blood Substrates in Human Plasma Based on Variable Selection Using Partial Least Squares (PLS) Regression Vector Choices," Fresenius' Journal of Analytical Chemistry, 362(1) (1998), 141-147.

Paul Stolorz, Alan Lapedes and Yuan Xia, "Predicting Protein Secondary Structure Using Neural Net and Statistical Methods," J. Mol. Biol. 225 (1992), 363.

M. Stone and R.J. Brooks, "Continuum Regression: Cross Validated Sequentially Constructed Prediction Embracing Ordinary Least Squares, Partial Least Squares and Principal Components Regression," Journal of the Royal Statistical Society B, 52, (1990), 237-269.

International Technology Roadmap for Semiconductors, 1998 Update.

The Jargon Dictionary, http://www.netmeg.net/jargon/terms/m/moore_s_law.html.

R.K. Lowry et al., "Plastic Encapsulant Materials Consistency for Reliability Assurance," Pros. ISTFA, Nov. 1995, 101.

Green, B. et al., "Evaluating the 'Labeled Magnitude Scale' for measuring sensations of taste and smell", Chemical Senses, 21, 1996, p. 323-334.

Zhang, L. et al., "Sensory evaluation of commercial truck interiors", SAE Technical Paper Series, 1999-01-1267.

* cited by examiner

METHOD AND APPARATUS FOR MONITORING MATERIALS USED IN ELECTRONICS

FIELD OF THE INVENTION

This invention relates to a method and apparatus suitable for monitoring selection, production, testing and use of electronic, assemblies, devices and the materials used therein.

BACKGROUND OF THE INVENTION

Several sensor technology developments have been described in the art. In particular, arrays of semiconductor sensors having sensitive and chemically-diverse interface materials capable of interacting with analytes of complex mixtures have previously been used. These can incorporate many operating principles including: doped tin-oxide gas sensors, doped conductive polymers, field effect transistor (FET) devices, and optical fiber devices.

Some sensors are based on a more specific chemical adsorption. For example, selective coatings or other surface modifications can be added to sensors such as immuno FET's, redox enzyme electrodes, ion-channel simulating devices or coated piezoelectric or surface acoustic wave devices [review by Gardner J. W., Bartlett P. N., Sensors Actuators, B18–19, 211–220, 1994]. Recently, mass sensing quadrupole transducers (e.g., using mass spectrometers (MS)) have been commercially available for the application in food quality control. MS can analyze sample headspace [U.S. Pat. No. 5,363,707 to Augenblick, et al.].

Other work and examples of devices used in the art of chemical sensing are described into the following references, which illustrate some of the major transducing systems such as (i) resonant microstructures [U.S. Pat. No. 5,025,346 to Tang, Williams C. and Howe, Roger T.; U.S. Pat. No. 5,445,008 to Wachter, Eric A. and Thundat (using a micro-cantilever), Thomas G.; Barnes J. R., et al., Rev. Sci. Instrum., 65(12), 3793–98, 1994], (ii) amperometric, conductivity/capacitance sensing platforms [U.S. Pat. No. 5,801,297 to Mifsud J.-C. and Moy L.] or (iii) optical detection [U.S. Pat. No. 5,563,707 to Prass Werner, et al.,; U.S. Pat. No. 5,512,490 to Walt David R. and Kauer John S.; U.S. Pat. No. 5,004,914 to Vali, Victor, et al.; U.S. Pat. No. 5,436,167 to Robillard Jean J.; U.S. Pat. No. 5,015,843, Seitz, William R. and McCurley, Marian F.].

In particular, the last approach can be illustrated by the development efforts of Walt, et al. [Dickinson T. A., White J., Kauer J. S., Walt D. R., Nature, 382, 697–700, Aug. 22, 1996] employing a miniaturized array of fibers containing a special fluorescent dye (Nile Red) embedded in a polymer matrix. Such a strategy is based on the use of a dye exhibiting large wavelength shifts in its strong fluorescent response to various vapors. The dye is photochemically stable and can be immobilized in polymers. The art uses a configuration of nineteen 300 $\mu$m optical fibers with their flat sensing ends coated with the dye (i.e., Nile Red) encapsulated in various polymers. A video frame grabber permits fluorescent intensity versus time data to be recorded. From the variations in response time and the individual fiber light output, the system can be trained to recognize these differences and identify specific vapors. One particular problem with the above-described system involves the photobleaching of the dye molecules. This limits the reliability and reproducibility of the sensor system.

Efforts to date in the art of gas sensor technology have centered upon the field of applications of the detection of toxic substances and smells for the evaluation of odor properties in consumer products, environmental science, and medicine [U.S. Pat. Nos. 5,801,297 and 5,563,707]. For example, microorganism detection in the manner described by Payne, et al./. in U.S. Pat. No. 5,807,701, uses an array of conducting polymer sensors to sample vapor associated with the microorganisms.

Almost all analytical techniques or process monitoring techniques are based on one or two variables at a time. For example, these variables can be an analytical signal representing absorbance, chromatographic retention time, or electrochemical response. These variables can be time-based as in process control. These traditional analytical techniques usually give acceptable results when analyzing simple systems with only a few components with variables (e.g., analytical signals) that do not interact with each other. Multicomponent mixtures such as solutions, gases, solids, process streams, effluents, and contents of reaction chambers usually have many variables that interact with each other. For example, absorbance peaks of several components can overlap each other. These variables should be analyzed simultaneously to optimize the useful analytical data that would be obscure in traditional analytical techniques.

As explained below, multicomponent mixtures or solutions can be analyzed by a multivariate analysis based on the reference data. {H. M. Heise, A. Bittner, "Multivariate calibration for near-infrared spectroscopic assays of blood substrates in human plasma based on variable selection using partial least squares (PLS) regression vector choices, Fresenius' Journal of Analytical Chemistry, 362(1) (1998) 141–147}. Nonlinear multivariate calibration methods have been reviewed by Sekulic, et al. (Analytical Chemistry, 65 (1993) 835A–845A).

Multivariate analysis techniques include many artificial intelligence techniques. Some examples include artificial neural networks (ANN), expert systems (ESs), fuzzy logic (FL), genetic algorithms (GAs). ANNs learn by training. ESs are based on defined rules. FL systems are based on uncertainty and partial truths. These techniques can be used in concert.

Isidore Rigoutsos and Andrea Califano in U.S. Pat. No. 5,752,019 and related references describe a family of new techniques using probabilistic indexing algorithms such as Fast Look-up Algorithm for String Homology (FLASH), hash algorithms, and data mining algorithms. Paul Stolorz, et al. describe Bayes algorithms (also called Bayesian statistical methods) in "Predicting Protein Secondary Structure Using Neural Net and Statistical Methods" J. Mol. Biol. 225 (1992) 363.

Multivariate analysis reconstructs analytical data from several variables. Multivariate process monitoring handles noise and drift better with fewer false alarms than univariate monitoring. For example, multivariate analysis can determine an analyte's concentration from several of its absorbance peaks. Theoretically, multivariate analysis can be applied to most analytical and process control techniques. Examples include: fluorescence, chromatography, absorption spectroscopy, emission spectroscopy, X-ray methods, radiochemical methods, nuclear magnetic resonance spectroscopy, electron spin resonance spectroscopy, surface science techniques, refractometry, interferometry, mass spectrometry, gas density, magnetic susceptibility, electrochemistry, surface acoustic wave sensors, sensor arrays, ultrasonic sensors, and thermal analysis.

Multiple variables can be converted into useful analytical data by multivariate analysis. This multivariate analysis or multivariate technique can relate instrumental response to the concentrations, physical, chemical, or physico-chemical properties at several wavelengths. Physico-chemical is defined as any combination of physical and/or chemical properties.

There are also the factor-based or bilinear projection methods of PLS, sometimes called Projection to Latent Structures, Principal Components Analysis (PCA), and Principle Components Regression (PCR). PLS is a good technique for process control when both process and product data are used to control the process. {Stone, M. Brooks, R. J. (1990) "Continuum Regression: Cross-validated Sequentially Constructed Prediction Embracing Ordinary Least Squares, Partial Least Squares and Principal Components Regression", Journal of the Royal Statistical Society B, 52, 237–269}. Nonlinear Principle Components Regression (NLPCR) and Nonlinear Partial Least Squares (NLPLS) can model nonlinear responses. {Sekulic, et al., Analytical Chemistry, 65 (1993) 835A–845A}. Soft Independent Modeling of Class Analogy (SIMCA) is another of several more multivariate methods.

The results of the multivariate analysis are usually used directly to give concentration values for the measured analyte. Multivariate techniques can be used for infrared and near-infrared spectroscopy. See James M. Brown, U.S. Pat. No. 5,121,337; Bruce N. Perry, et al., U.S. Pat. No. 5,641, 962. Perry, et al. Claim non-linear multivariate methods. Multivariate techniques can be used for hyphenated chromatography like GC-MS. Ashe, et al., U.S. Pat. No. 5,699, 270. Multivariate techniques can be used for surface acoustic wave (SAW) vapor sensors. Lokshin, et al. U.S. Pat. No. 5,465,608. Some references describe applying other properties to the data such as octane values. Bruce N. Perry, et al., U.S. Pat. No. 5,641,962; Maggard, U.S. Pat. No. 5,349,189, freezing point depression in milk, Arnvidarson et al., U.S. Pat. No. 5,739,034, and cancerous stages of tissue samples Haaland et al. U.S. Pat. No. 5,596,992.

Packaging costs for Integrated Circuits (ICs) are rapidly becoming the greater portion of electronics device costs. This refers to the printed circuit board, substrate, dies, wires, pins, and other connectors, etc. Encapsulation refers to the "plastic" material that ICs are embedded in by molding or other techniques.

The US National Technology Roadmap for Semiconductors estimates that packaging costs may exceed 50% of the total device product cost in 1998 [International Technology Roadmap for Semiconductors, 1998 Update, http//:www.itrs.net/NTRS/PubINTRS.nsf/pages/Home.htm]. The available I/O that can be handled using wire-bonding techniques is also reaching its density limit. Newer techniques such as TAB, flip-chip, and grid arrays are required as the chips continue to shrink and become more complex. Cost is driving packaging technology towards cheaper solutions while performance demands get tougher. This is defined by Moore's Law that observation that the logic density of silicon integrated circuits has closely followed the curve (bits per square inch)=$2^{((t-1962))}$ where t is time in years; that is, the amount of information storable on a given amount of silicon has roughly doubled every year since the technology was invented [The Jargon Dictionary, http://www.netmeg.net/jargon/terms/m/more_s_law.html].

The traditional approach for monitoring electronic component quality is a denaturating physical analysis which is both time consuming and limited in the amount of information provided. It is within the scope of this application to provide a non-destructive method and apparatus for probing the quality of semiconductor and encapsulant packaging materials that can cause failure of some internal features of an electronic device. For example, it has been reported that siloxanes can cause disk drive failure and can be detected from collected headspace [U.S. Pat. No. 5,918,289].

Most of semiconductor devices and in particular integrated circuit chips utilize packaging materials such as plastic encapsulants for encapsulation for physical protection and installation into electronic systems. Plastic molding compounds consist of typically 70–80% inorganic filler (e.g., silica) and 20–30% organic materials comprising resins, hardeners, stress relievers, coloring agents and other organic additives [Lowry R. K., Hanley K. L., Julien N., plastic encapsulant materials require consistency for reliability assurance, Proc. ISTFA, November 1995, p. 101]. Some practices in the prior art exploit pyrolysis infrared (IR) methods for identification of mold compound product types. Such a method consists in breaking an integrated circuit package sample and placing a piece of mold compound on an heating ribbon in a pyrolysis cell with ZnSe attenuated total reflectance (ATR) crystal. The chamber is then evacuated, the sample heated about 800° C. and then cooled down to allow organic volatiles to condense on the ATR crystal. Then, Fourier transform infrared (FTIR) spectrum of the mold compound can be acquired and the IR peak information allows to identify the compound type.

This application is related to application Ser. No. 09/332, 659 filed on Jun. 14, 1999 by F. Zenhausern and is incorporated by reference herein.

SUMMARY OF THE INVENTION

The method described in the present application can monitor outgassing of the materials using an apparatus comprising at least a multisensor array detector (e.g., mass spectrometer, solid-state gas sensors, optical sensors) generating preferably a multitude of signals which can be processed with a multivariate statistical algorithm. The output of said signal processing can provide a fingerprint of a processed materials and said fingerprint can be used to control the quality of said materials which may be important for further processing steps of the manufacture of an electronic device.

It is within the scope of the present invention to provide a method and apparatus for detecting organic volatiles and/or offgassing products from plastic encapsulant materials using an array of gas sensors and multivariate analysis. The detectable species can be normally volatile, or can at least partially be transferred to the sensors by heat, electromagnetic radiation (e.g., ultraviolet, infrared, microwave, radio frequency, laser pulses, etc.), ultrasonic vibration, or pressure variations. Pyrolysis can be used, but can damage the tested system.

DETAILED DESCRIPTION OF THE INVENTION

The present invention has as its object to provide a method and apparatus for mapping various components of an environment comprising preferably semiconductor and/or IC packaging that enable to predict the presence of minute quantities of offgassing volatiles comprising organic molecules, solvents or any interfering component which can preferably be correlated with physico-chemical parameters of said environment. For example, such an information can be used to assess the quality and/or performance of the semiconductor materials (e.g., failure analysis). There is no prior art applying gas multisensor arrays (MSA) combined with multivariate analysis to the monitoring of the quality of electronic packaging although near-infra-red measurements using multivariate calibration are routinely performed in the semiconductor industry. The determination of volatile Organic Compounds (i.e., VOCs) from parts of hard disk drives assemblies is often performed by a costly and destructive method comprising the use of gas chromatography/mass spectrometry (i.e., GC/MS) as it is described into industrial standard protocols [IDEMA Standards, Microcontamination, document No M8–98]. MSA technology is typically using metal oxides, conducting polymers and quartz crystal microbalance sensing elements. In the mostly used case of tin dioxides particles, the electric resistance increases in air due to its potential barrier but when the sensors are exposed to an atmosphere containing reducing gases, the tin dioxide surface adsorbs the gas molecules and causes oxidation. This lowers the potential barrier, thereby reducing the electrical resistance. The reaction at the interface is depending on the sensor temperature and the activity of sensor materials. Some volatiles can similarly adsorb and desorb at a conducting polymer surface, which causes changes in their electrical resistance. Often, the signals of an array of tin dioxide vapor sensors are used as inputs to a data analysis program (e.g., neural network and/or chemometrics software packages) to generate a pattern representative of the components of an odor or vapor mixture. In accordance with the principles of the present invention, there is provided a novel approach for probing the quality of electronic components. The present approach is distinct from the prior art and it is manifest in a novel method and apparatus suitable for probing at least the quality of a semiconductor material or an electronic component, the method comprising the steps of:

1) selecting a specimen from at least a part of an electronic assembly which is preferably comprising of semiconductor materials and/or electronic components,
2) collecting some outgassed compounds of said specimen preferably by headspace sampling,
3) carrying said headspace representative of the physico-chemical properties of said specimen to an analysis chamber preferably comprising a plurality of sensing units capable to interrogate at least one of said properties,
4) monitoring at least one signal which can be generated at a sensing unit when said headspace is carried out in close proximity to said sensing units,
5) processing any change which may be affecting at least one of the sensing units signals to identify a pattern representative of a profile of said outgassed compounds,
6) correlating said signals with the physico-chemical properties of said outgassed compounds using a multivariate analysis for generating an identification pattern, and
7) comparing said pattern with a reference specimen to assess the quality of said specimen.

The present invention as defined can realize several significant advantages. First of all, the novel method has a capability for generating qualitative, quantitative and time-responsive information that can be employed for developing in situ process manufacturing monitoring. To this end, the novel method can be selectively and variously employed, for example, in dependent steps, for:

1) identifying an appropriate raw materials specimen from a second raw materials specimen, or
2) discriminating a materials specimen with respect to at least one reference material, or
3) identifying a first component from a second component of an assembly, or
4) detecting an interference from a component potentially causing an operating failure of an electronic assembly.

The present invention also includes an apparatus for performing the novel method, the apparatus comprising the following elements: a sample collector (e.g., automated headspace sampling device); a fluidic method for carrying a carrier gas and/or analyte to a first analysis chamber preferably located in the path of the gas flow and being equipped with at least a sensing device that is capable to respond to the presence of at least an analyte; a sensor capable of generating at least one signal; and a display, on the basis of a change of at least one. physico-chemical properties of said sensing device, a quality (e.g., presence) and/or quantity (e.g., concentration) of the analyte. Static headspace or dynamic headspace sampling (e.g., using a carrier gas) can be used.

Ratios of vapor pressures of various species in the tested system can be manipulated or compensated for to affect each other. The interaction between the species and the mother matrix from which they came can be investigated to provide indirect measurement of the matrix itself as well as the daughter species or byproducts themselves. For example, the curing stage of a two part epoxy can be monitored by detecting the high vapor pressure monomer from one resin and the high vapor pressure hardener that have partitioned into the gas phase at particular temperatures and times. This method can be extended to more complicated formulations typical of the electronics packaging industry. The structure, morphology, chemistry, and properties of the mother matrix can affect partitioning of individual analytes from the matrix into the gas or vapor phase where they can be detected. In this way, these properties of the matrix can be indirectly modeled.

A superconductor or other material with temperature-critical operation can be monitored by detecting changes in gas concentration or flow rates. Rates of nitrogen or helium boiling are one example. Outgassing or pyrolysis products of impurities in the superconductor can be analyzed before or during usage.

In another example, profiling "electronic smells" has recently emerged as a promising technology for the rapid identification of odorous molecules in chemistry, consumer products, environment and medicine. The development of analytical instrumentation based on gas detection is currently using an array of solid state gas detectors combined with an automated pattern identifier. Such odor detection systems are commercially referred as an electronic or artificial nose [U.S. Pat. Nos. 5,801,297; 5,675,070].

The term integrated circuit herein refers to assemblies of electronic components and conductive connectors in supported relation (e.g., on a board). In a particular aspect, this invention provides urethane polymer compositions useful to encapsulate integrated circuits to protect such circuits from shock and stress, which compositions are: free of contaminants; readily applied by automated processes including use of robotic dispensers; fast and conveniently curable; tack-free curing; non-absorptive of ambient moisture; dimensionally stable under processing conditions sufficiently to not unduly stress the attachment of the integrated circuit chip to the board substrate, the attachment of the encapsulant to the chip including at the edges and corners thereof, the attachment of the encapsulant to the board substrate, or the attachment of the encapsulant to projecting wires and wire attachments; resistant to deterioration when immersed in hot solder; and, free of bubble-induced failures, the so-called "popcorning" when heated rapidly in a solder immersion bath, even after continued exposure to ambient high humidity.

Semiconductor chips and their encapsulating packages are made from a wide variety of organic and inorganic materials. Obtaining information about chemical composition of electronic devices, the substances used in their manufacture, and foreign materials or contaminants is essential to sustaining manufacturing processes improving manufacturing yields, and ensuring quality and reliability of microcircuit devices. It is within the scope of the present invention to describe a new method and apparatus for the analysis of preferably gas-phase chemical reactions or volatile substances typically releasing (e.g., off-gassing products) from semiconductor materials and/or IC packaging, to provide a "fingerprint" or pattern characterizing, for example, the quality of said materials as well as possibly the concentration of some contaminants.

It is another object of the present invention to analyze of bond pad contamination. Most of the semiconductor chips have an array of open aluminium areas along their edges or "bonding pads", where aluminium or gold wires from the leads of an encapsulating package are attached to connect the IC to external systems, for example. As the aluminium pads are not protected by any passivation layer, contamination may occur [Lowry R. K., Linn J. H., characterizing IC bond pads, Proc. Int. Symp. For Testing and Failure Analysis, 1992, p165]. It is well known by those skilled in the prior art that such surface contamination of the bonding pads can be analyzed by FTIR microscopy whose spectra can allow to determine the nature of the contaminants that may influence the performance or reliability of a product or its processing. However, there are very little efforts focusing on developing new method or apparatus for qualitative and/or quantitative analysis of semiconductor device components and/or contaminants. Typically, plastic encapsulation is monitored by FTIR analysis for manufacturing process development [Shala F. J. Applications of FTIR microspectroscopy in contamination analysis, Proc. Int. Symp. For Testing and Failure Analysis, 1992, p175].

BRIEF DESCRIPTION OF THE DRAWINGS

In the interest of clarity, the following detailed description of a preferred embodiment is illustrated in the accompanying drawings, in which like reference numerals refer to like parts in which.

Figure 1:
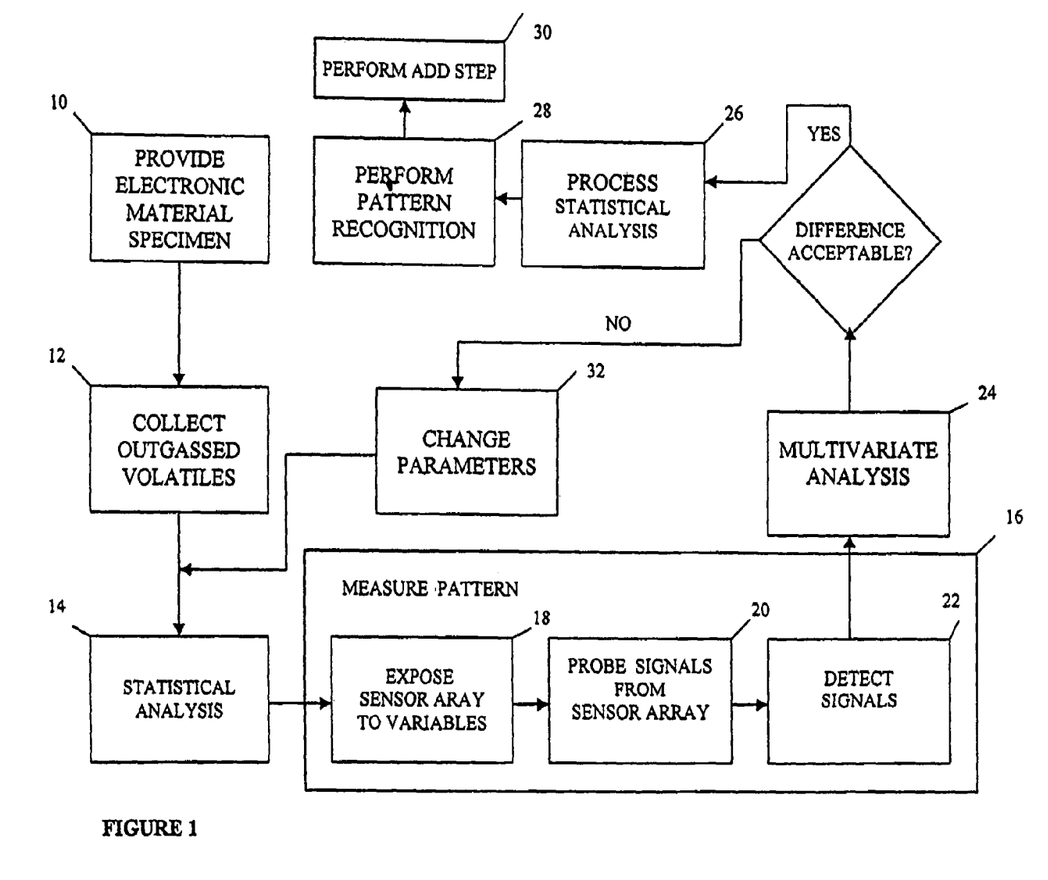
FIG. 1 shows a flowchart which illustrates some steps for realizing the novel method.

Attention is now directed to FIG. 1 which shows a schematic overview of the steps that preferably may be used in the realization of the present invention, in particular, for characterizing the quality of an electronic component which can be part of a more complex electronic device.

For example and as it is seen in FIG. 1, in the manufacture of semiconductor integrated circuits, a semiconductor specimen and/or electronic component is often provided (step 10) as a part of an electronic assembly (e.g., a hard drive disk). The novel apparatus is readily used for measuring (step 12) outgassing headspace comprising typically organic volatiles. Such outgassing compounds are than compared (step 14) with pre-selected values (e.g., threshold concentrations). Process parameters, preferably incubation time and/or temperature, outgas sampling volume which have been initially set (step 16) are readily adjusted (step 16) to bring measured values within some signal tolerances, for example, such as normalized sensor intensities (i.e., $\Delta R/R_0$ in the case of metal oxide sensors) greater than 10%. Additional steps (18) toward completion of a manufactured electronic article are then performed based upon some decision criteria (e.g., pattern) exploiting qualitative information generated by the novel method. The measuring step includes carrying outgases (step 20) to a sensor array adjusted to detect some changes in the sensor responses (step 22) when exposed to the gas phase, and process to signal processing (step 24). The output of such an apparatus is then interrogated in view of either feedback some analytical parameters (step 26) or to proceed with multivariate analysis (step 28) such as pattern recognition (step 30) to assist in further characterization of said semiconductor material or electronic component. Typically, operating failure can be detected or predicted and manufacturing adjustment can then be performed to optimize the quality of the electronic article comprising in part or whole the electronic semiconductor material.

Figure 2:
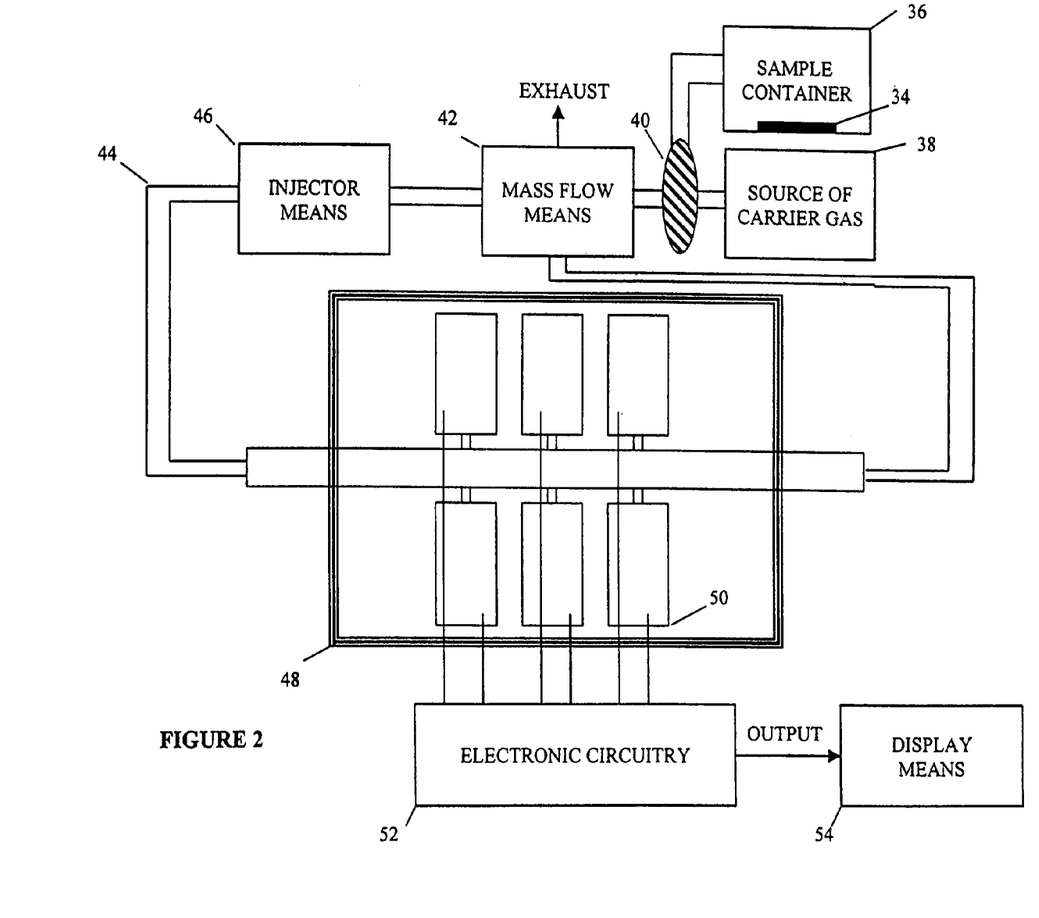
FIG. 2 provides a schematic of a preferred embodiment employed to realize the invention.

FIG. 2 is a schematic diagram illustrating a preferred embodiment and is not drawn to scale. For example, a specimen 34 is disposed into a container 36 which can be placed in close proximity to a heater (e.g., heating block, not shown) with a power supply for thermally heating the specimen. In operation, a headspace is evolving from the specimen, which comprises typically outgassing compounds that can be collected in a gas syringe or mixed up through a tubing with a carrier gas. The carrier gas can be delivered by a source of ultrapure gas 38 which can then be mixed with the outgasses via a valve 40 connected to a mass flow controller (MFC) unit 42. The MFC can pressurized the system fluidic 44 to assist in delivering a desired gas dilution when a sample is injected with an injector port 46 to the chamber analysis 48. The chamber 48 includes preferably an array of sensors (e.g., using similar and/or different transducing mechanisms) 50 controlled by an electronic circuitry 52. The output signal from the electronic circuitry 52 can then be processed and displayed with a display 54 such as a computer.

Figure 3:
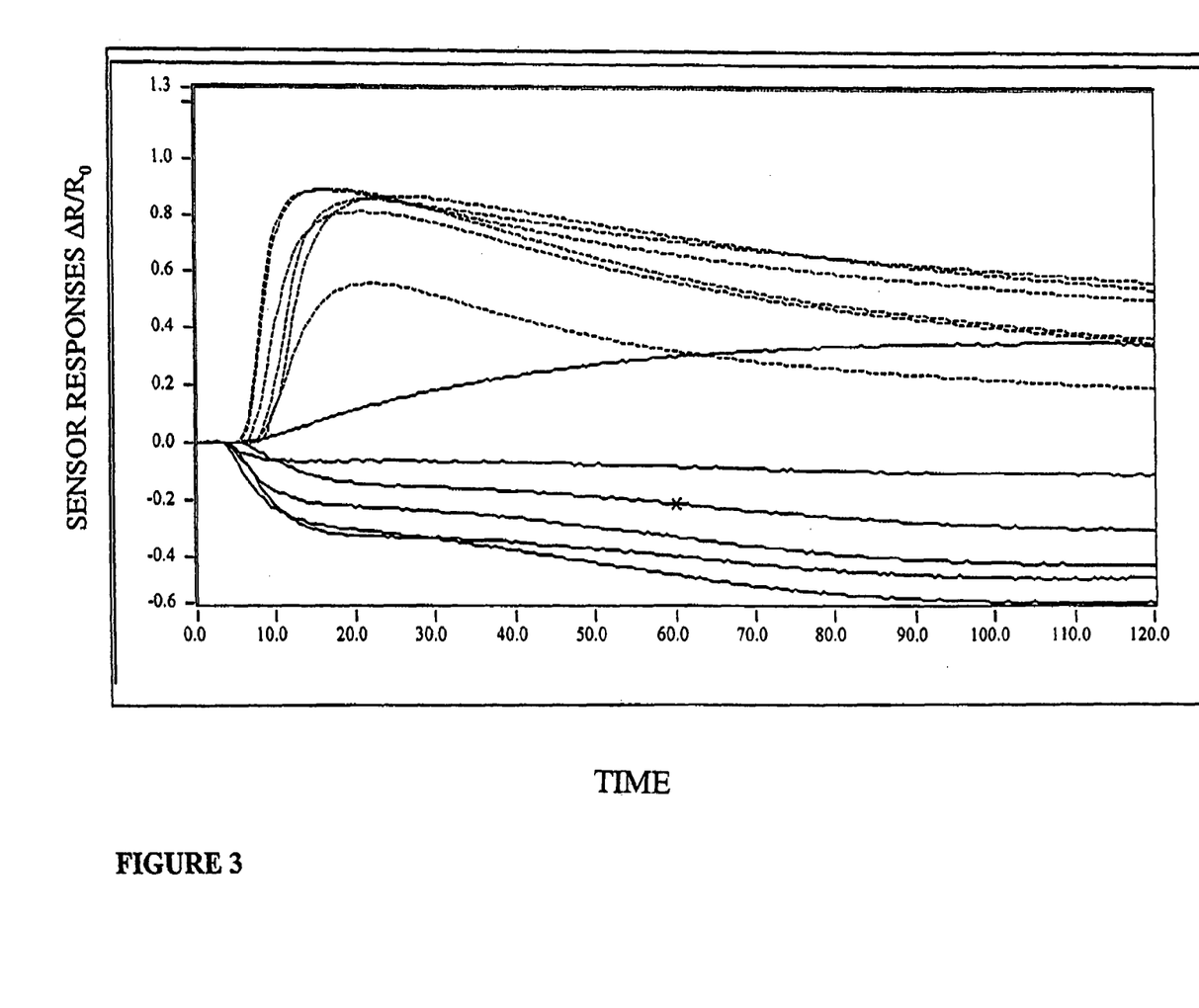
FIG. 3 is a plot of the sensor response of 12 metal oxide sensors ($\Delta R/R_0$) over time.

FIG. 3 shows a graph of individual responses of multiple sensors when exposed to the analytes. Each individual sensor is a separate line. There are two groups of six metal oxide sensors. Each group is doped differently. One group exhibits negative signals and the other group exhibits positive signals. The x axis is time in seconds. In this example, the Y axis is the normalized change in sensor resistivity. These responses comprise several of the data points used in FIG. 4. Specifics are given in Example 1.

Figure 4:
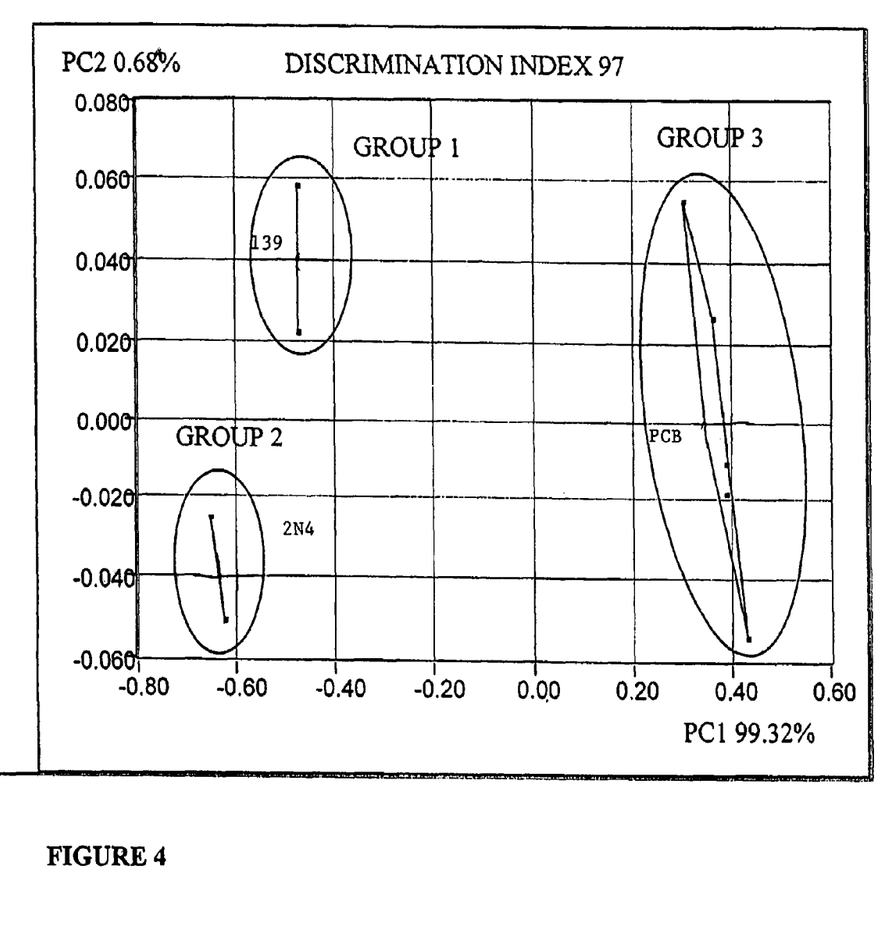
FIG. 4 is a two dimensional plot of a multivariate analysis output using a principal component algorithm.

FIG. 4 shows a "fingerprint maps" using PCA multivariate analysis. These groups represent three different electronic components used in Example 1. The groups are well separated showing good discrimination. There is more separation along the X axis resulting in a larger separation distance between group 3 (a circuit board) and groups 1 and 2 (semiconductor components).

The invention relates to apparatus and methods for monitoring or probing information in a medium having at least one component of a material or assembly used in electronics. The medium is screened or analyzed (preferably in its gas phase) by coupling a sensor responsive to concentrations or changes of the medium and/or secondary products and/or byproducts. The terms monitoring and probing can be used interchangeably in this application. For example, this invention can monitor a process or can monitor a volatile analyte outside of a process.

In particular, the invention pertains to the method for monitoring information in a medium, the medium having at least one analyte, the method having the steps of screening the medium with a sensor or screening device having a n number of sensing probes, where n is an integer of at least one so that more than one physical, chemical, or physicochemical change which defines the information is detected by the probe to produce at least one signal output; transferring the signal output to a signal processor capable of multivariate analysis responsive to differences in electromagnetic properties of the signal for generating a final output; receiving the final output into a pattern recognition program sufficient to generate a measurement pattern of the information being operable to define a set of class boundaries; and sorting the information in accordance with the class boundaries representative of the presence and preferably quantitative amounts of analyte in the medium. The medium can be a gas or a liquid or a solid or a combination of several phases. The medium can have at least one of organic or inorganic reagent.

The n number of sensing probes can be a multiple sensor array. The n number of sensing probes can also be at least one semiconductor gas sensor, doped metal oxide gas sensor or an undoped metal oxide gas sensor used in gas or vapor phase, conductive polymer sensor, vibrating or resonant micromechanical device, mass spectrometer, or optical sensing probe (e.g., an optical fiber, apertured probe, and/or apertureless probe). The sensing probe can also have one or more coatings.

The information can be at least one of odorous or volatile chemical species characteristics of the presence of the analyte or the part of the analyte. At least part of the information detected by the probe can be changes in the concentration of the analyte, a secondary product of the analyte, a radiative property of the electromagnetic spectrum of the analyte, a non-radiative property of the electromagnetic spectrum of the analyte, or a non-radiative property of the electromagnetic spectrum of a secondary product of the analyte.

The multivariate analysis can be principal components analysis, deterministic finite-state automata, or partial least squares. The multivariate analysis can be trained, or supervised, or untrained, or unsupervised. The signal processor or multivariate analysis software can be a frequency analyzer.

This method can further have the steps of obtaining a multivariate analysis reference model based on the signal output; and screening an analyte selected from the group consisting of a analyte, a analyte fragment, a analyte byproduct, a medium, a reagent, and a tag, to predict the property of the analyte. This method can also further have the step of comparing the class boundaries with properties of a second group of signal outputs. Both quantitative and qualitative models can be used as part of this invention. New multivariate analysis techniques will also be developed, and are contemplated to be used in this invention.

This invention includes an apparatus for analyzing at least one analyte in a medium, having a multivariate detector having at least one of a sensing probe, sensing location, or physicochemical property, said multivariate detector capable of detecting at least the analyte, a byproduct, or a secondary product thereof, and discriminating the analyte, the byproduct, or the secondary product from the medium; wiring or other transmission means, capable of transmitting a signal between the multivariate detector and a data acquisition system, capable of converting the signal into raw data; a computational device capable of processing at least part of the raw data using multivariate analysis to create a data set; and an output device capable of displaying, storing, or using the data set. The output device can be or include a feedback control capable of using the data set to control a biological replication process. This analyte can come from any component, assembly, and/or processing aid used in electronics, and the feedback can control production, processing, storage, modification or use of the analyte in approximately real time.

The above specific medium types sensor probe types, analysis types, analyte types, and information types are preferred embodiments of this invention and only the claims should limit this invention. In one embodiment (illustrated by FIG. 1), the system includes at least one sensing device and circuitry (i.e., electronics) for monitoring an induced signal. It will be appreciated that the sensing device may be relatively uniform or have different sensing areas. An assembly or hybrid of similar or different sensing devices may also be used. Other systems and methods may be employed, such as the use of mass spectrometry (MS) for the analysis of the sample headspace, providing a sensing apparatus and methodology for detecting and evaluating at least one analyte alone or in an admixture.

An MSA is made up of at least two different sensors. Often each sensor in the array has its own signal connection and its own sensitivity. However, other MSA configurations are possible. For example, one can scan a sensor with a non-uniform sensing surface.

Sensors can be based on many different technologies. Examples include, but are not limited to: sensor materials, sensing mechanisms, communications methods (e.g., wireless), sensing discrimination, and useful lives. The invention can use many technologies including, but not limited to: metal oxide semiconductor (MOS), quartz crystal microbalance (QCM), mass spectrometry (MS), surface acoustic wave (SAW), aperture (e.g. fiber optical sensors) or apertureless optical sensors (e.g. sharp resonant microcantilevers such as the ones used in AFM), interferometric sensors, scanning probe techniques and its modifications (e.g., porous silicon, photoluminescent, and GaAs), chemically-sensitive field effect transistors (chemFET), electrochemical sensors, sensors modified with conductive polymers, and pressure sensors. Scanning probe techniques include methods and instruments such as atomic force microscopy (AFM), scanning tunneling microscopy (STM), and scanning interferometric apertureless microscopy (SIAM). Apertured probes, including many fiber optics probes, use lenses and are diffraction limited. Apertureless probes, such as probe antenna and SIAM {Wickramasinghe, et al., in U.S. Pat. No. 5,646,731 and U.S. Pat. No. 5,538,898; and Zenhausern, et al. in Science, 269, pp. 1083–1085 (1995)}, use local perturbation of electromagnetic fields instead of lenses.

A sensing probe can be any sensor, instrument or other means for detecting chemical, physical, or physico-chemical changes of a analyte, part of a analyte, or their related by-products, solvents, medium, reagents, and environment.

Resonating or vibrating sensing probes are defined as micromechanical devices such as SAW, QCM, AFM cantilevers, and materials with piezoelectric properties. Resonating sensing probes are preferred. These sensing probes can be coated with materials such as polymers, ion exchange resins (e.g., perfluorosulfonated ionomers called PFSIs), porous silicon, optical reflectors, silanes, thiols, oxides, absorbents, selective coatings, chromatographic solid phases (e.g., for gas chromatography), hydrocarbons, elastic coatings, hygroscopic materials, cage materials (e.g., buckyballs and fullerene tubules), crown materials (e.g., crown ethers), or nucleotides. The coating can be in thin films, monolayers, sub-monolayers, self-assembled monolayers (SAM) and other formats. Part of the coating can contain binders, and/or physical fillers.

Liquid phase MSA detectors can often be less sensitive due to the usually higher analyte concentrations found in a liquid compared to a vapor. In comparison, gas phase detection usually offers an added level of selectivity by monitoring liquid to gas transitions and less surface contamination (i.e., longer useful life and often faster response time). Combining volatilization methods such as mass spectrometry or electrospray with a gas phase MSA (often called an electronic nose) would greatly benefit the detection of large analytes such as polymers or oligomers.

Multivariate analysis can be based on many different technologies including, but not limited to: classical least squares (CLS), inverse least squares (ILS), partial least squares (PLS), principal components analysis (PCA), principle components regression (PCR), nonlinear principle components regression (NLPCR), nonlinear partial least squares (NLPLS), deterministic finite-state automata (DFA), FLASH, pattern recognition, and neural networks. The multivariate analysis can be trained/supervised by teaching it what signals to use based on theory or analyte samples of known parameters. Alternatively, multivariate analysis can be untrained/unsupervised.

This invention covers measurement in solid (e.g., temperature, mass, cantilever, and tactile measurements), liquid, gaseous, and vapor (e.g., aerosol) phases. Solid phase sensing is rare. Liquid phase measurements tend to be prone to sensor fouling. Immersed sensors also tend to have less selectivity than gas or vapor phase sensors. By measuring in the gas or vapor phase, MSAs can have an added layer of selectivity base on which molecules enter the gas or vapor phase. In this way, the contents of a headspace can be a subset from the contents of the condensed phase it is in contact with.

In a preferred embodiment, a multivariate detector can preferably comprise an array of sensing devices which might be using similar or different transducing mechanisms. As it has been described earlier in the present application, several sensing devices can be used to monitor components used in electronics. In particular, an assembly of a few metal oxide electrodes (e.g. $SnO_2$) can have some of their physicochemical properties modified when they are exposed to a medium comprising molecular species (e.g., monomers, silanes, siloxanes, or oligomers) and/or reagents and/or by-products. Such modifications can be probed with and electronics generating a set of output variables which are then processed and analyzed using multivariate algorithms. Such a electronics is preferably a multivariate detector.

It is also within the scope of the present invention to offer a novel alternative technology for measuring components and processing aids used in electronics, preferably using a number of gas sensors often organized in arrays, and a recognition means (e.g., pattern recognition) typically exploiting multivariate analysis algorithms (e.g., PCA, DFA, SIMCA, PLS). Representative examples are described above. The embodiment described further in this invention can achieve real-time detection of molecular species. The preferred time period between detection samples is less than about 70 milliseconds. This real time detection does not have to include analysis time.

Based on the needs for improvement, it is also within the scope of this invention to monitor any material used as a component in electronics or in the production of electronics with the use of at least one sensor capable of being responsive to any change of its photophysical and chemical properties by influence of surface interactions. Preferably, electroluminescence and photoluminescence quenching or spectral shifts of porous silicon sensor material [Sailor, M. J., Lee, E. J., Advanced Materials, 9(10), 783–793, 1997; U.S. Pat. No. 5,453,624 to Sailor, Michael J. and Doan, Vincent V.] should permit simple and cost-effective sensor fabrication. The pore diameter affects the wavelength. There is no photobleaching as with dyes and both wavelength and wavelength shifting can be measured. All references above are incorporated herein by reference in their entirety.

Data storage disk drives could benefit from this invention. Examples include hard drives, compact disk drives, optical drives, magneto-optical drives, CD-R drives, and similar data storage devices. A fiber optic sensor is integrated into a hard drive flying head assembly. The tip of the fiber optic sensor is coated with a fluorophore-embedded polymer as described by Walt, et al., in U.S. Pat. No. U.S. Pat. No. 5,512,490. The coating is sensitive to at least one contaminant. Typical contaminants include anions (e.g., chloride, sulfate, nitrate, phosphate, etc.), cations (e.g., sodium, potassium, calcium, magnesium, ammonium, cobalt, nickel, etc.), organic acids (e.g., formic, oxalic, acrylic, benzoic, 2-ethyl hexanoic acid, etc.), siloxanes, oxides, sulfur compounds, organics (e.g., DOP, amines, amides, vinyls, organophosphates, organosilicates, lubricants, etc.), water, and particulates (e.g., diamond, silicates, alumina, magnetic particles, etc.). Surface defects and thermal-asperity inducing local temperature changes may also be detected by related changes in the partition coefficient of the volatiles.

During rotation, the air flow (e.g., Bernoulli flow) agitates the gas and particulates within the hard drive and cause them to pass over the surface of the sensor. The sensor may also inspect the surface of the disk medium (e.g., for oxidation and/or defects).

A 632 nm laser illuminates the fiber optic to activate the fluorophore and optionally illuminates the disk medium. The illumination mode can be in the near field or far field regime. A filter or split fiber separates out the incident illumination 632 nm light and its possible harmonics from the returned optical signal. A avalanche photodiode (APD) or photomultiplier (PMT) detector converts the optical signal to an output signal. Optionally, this output signal is multiplexed with electrical information from the read/write head.

The output signal is analyzed with graphical multivariate analysis software. During a continuous real time operation, the output signal is processed and compared to a reference fingerprint pattern or map or library. Both the presence of compounds or their absence can be significant. Usually the matrix or media itself is not analyzed directly. Additives, contaminants, byproducts, tags, and other secondary materials are usually detected. From these secondary materials, information about the matrix can be modeled. During normal operation a signal can be recorded and projected against the reference and characterized. Tags can be added to a test system for purposes such as marking, too low analyte gaseous concentrations, time tracking, etc.

Results are compared to a fingerprint library of known contaminants, known changes due to surface defects, the contents of the hard drive under normal operating conditions, corrosion products, water buildup, temperature-induced volatiles, crash-induced particulates, etc. A typical test includes fly stiction (static friction between the slider and the stationary disk) and meniscus-effects occurring in drives operating continuously for 100 days of 92% random read/write and 8% sequential read/write. Droplets forming on the heads and media of drives are analyzed by the sensor to characterize bearing grease and smaller quantities of contaminants listed above. In another important application, chemical profiling or analysis of the interface stiction can be performed directly in real time by the present invention.

For example, multivariate analysis of the combination of siloxane, bearing grease, and particulate concentrations during normal operating conditions can graphically portrayed in a graph similar to FIG. 4. During test or field operations, siloxane, bearing grease, and particulate concentrations can be compared to the combination of siloxane, bearing grease, and particulate concentrations detected by the sensor. The ability to analyze combinations of analytes instead of having to separate and identify individual signals is a major advantage of this invention. For example, tribology conditions can be optimized.

Results from the multivariate analysis can be logged over long times such as 100 hours to 5 years in test environments, accelerated aging, normal use, and specialized applications. These data logs can be used to improve future electronic products or can be used directly to affect the devices usage and performance. Time effects can be built into libraries, to asses aging, to asses kinetics, etc.

This invention includes the following. A method for probing at least the quality of a material used in electronics or optics, the method comprising the steps of: measuring an analyte selected from the group consisting of the material, a constituent of the material, a byproduct of the material, and a reaction product of a constituent of the material, and a tag; detecting more than one physical, chemical, or physico-chemical property of the analyte; combining the property to produce a signal output; processing the signal output with multivariate analysis to convert the signal output into information representative of a quality of the material, a constituent of the material, or processing of the material.

The method above, wherein the multivariate analysis comprises processing the signal output with a pattern recognition means sufficient to classify, compare, or discriminate the material based on at least one member selected from the group consisting of quantity, quality, performance, physical, chemical, physico-chemical properties, environmental effects, or timing effects. In this method multivariate analysis can use either unsupervised statistical pattern recognition or supervised statistical pattern recognition.

In the above methods, the analysis can be at least one member selected from the group consisting of classical least squares (CLS), inverse least squares (ILS), partial least squares NLPLS), principal components analysis (PCA), principle components regression (PCR), nonlinear principle components regression (NLPCR), nonlinear partial least squares (NLPLS), deterministic finite-state automata (DFA), Fast Look-up Algorithm for String Homology (FLASH), pattern recognition, and neural networks.

In different applications of the above methods the quality analysis consists in sensory evaluation of the sample materials by human paneling. The near-field probe can include a coated optical fiber. The analyte is preferably a gas, a vapor, or suspended in a gas, optionally collected by a static or dynamic headspace technique. A mixture of analytes can be screened, and the signal output represents the overall properties of the mixture. At least one member of the group consisting of heat, electromagnetic radiation, electricity, magnetism, and mechanical vibration at least assists in transferring the analyte from the material to a gaseous or vaporized form.

The gas sensing means can comprises at least one member of the group consisting of a semiconductor gas sensing device, a conductive polymer gas sensing device, a surface acoustic wave gas sensing device, a microbar sensing device, a micromechanical probe, a quartz crystal microbalance, and an optical sensor. In a preferred mode the gas sensing means comprises at least a metal oxide semiconductor gas sensing device.

The method of this invention can monitoring a process of preparing or assembling parts into an electronic assembly, comprising the steps of: collecting a gaseous or vaporized species from at least one member selected from the group consisting of a circuit board, a solder paste, a solder, a solder flux, an epoxy, a conductive epoxy, a resin, an electronic component, a discrete component, a thermally conductive paste, an adsorbent, an encapsulant, a coating, a filler, a lubricant, a reactant, a byproduct, a contaminant, and a tag; screening at least one of the gaseous or vaporized species with a screening means comprising a n number of sensing probes, where n is an integer of at least one so that more than one physical, chemical, or physico-chemical change which defines the information is detected by the probe to produce at least one signal output; and analyzing the signal output with multivariate analysis to convert the signal output into information representative of the process and or its components.

The part above can preferably be a circuit board (e.g., as in a soldering operation or surface mounting with conductive epoxy) or a multichip module. The contaminant is usually at least one member of the group consisting of anions, organic acids, organics, and particulates. The above methods can further comprise the step of using the information in a feedback loop to control the process.

This invention includes a method for monitoring a process of packaging or encapsulating a material used in electronics or optics with a package or encapsulant, comprising the steps of: collecting a gaseous or vaporized species from at least one member selected from the group consisting of the material, the package, and the encapsulant; screening at least one of the gaseous or vaporized species with a screening means comprising a n number of sensing probes, where n is an integer of at least one so that more than one physical, chemical, or physico-chemical change which defines the information is detected by the probe to produce at least one signal output; and analyzing the signal output with multivariate analysis to convert the signal output into information representative of at least one ember selected from the group consisting of the process, the material, the package, and the encapsulant.

The material and the package can be part of at least one member selected from the group consisting of an integrated circuit, a multichip module, an optoelectronic device, an integrated circuit board, a memory module, and an electronic device. At least one analyte can be water or residual solvent and the information can represent the degree of popcorning. The encapsulant can be a water barrier or a moisture barrier.

This invention can also monitor or probe at least the quality of a material used in electronics or optics, the method comprising the steps of: selecting a sample of the materials from a storage environment or a manufacturing process; collecting a gas from the sample; analyzing the gas with n number of sensing probes, where n is an integer of at least one so that more than one physical, chemical, or physico-chemical property detected by the probe and combined to produce a signal output; performing a multivariate analysis on the signal output to characterize the material, the storage environment, or the manufacturing process.

The above method can include the step of selecting a component or processing aid used in plastic molding compounds. For example, this can be selecting a semiconductor materials comprising insulating dielectric materials, or selecting a semiconductor materials comprising a modified silicon wafer. The plastic molding can consist of about 45% to about 95% inorganic filler and about 5% to about 55% organic materials. The inorganic filler can consist of silica. The organic materials can include resin compounds, hardener, or catalyst compounds. The material can include a semiconductor, an oxides, a superconductor, a plastic, or a composite.

This invention includes a method for characterizing an electronic device, the method comprising the steps of: screening the electronic device with n number of sensing probes, where n is an integer of at least one so that more than one physical, chemical, or physico-chemical property detected by the probe and combined to produce a signal output; processing the signal output with multivariate analysis to convert the signal output into information representative of the device, an operating characteristic of the device, or a property of the device.

The above method can further analyze electronic signals in the device and n can be an integer greater than one. This method can use information to control the device. The screening can be of a gas or a vapor within the electronic device. Sample operating characteristics are device performance, optimization, analysis, or failure prediction according to device specification. Sample devices are a data storage disk drive or a component within the data storage disk drive.

This invention also includes an apparatus for probing at least the quality of a material used in electronics or optics, comprising: a multivariate detector having at least one of a sensing probe, sensing location, or physicochemical property, the multivariate detector capable of detecting an analytes that is at least one member selected from the group consisting of the material, a constituent of the material, a byproduct of the material, and a reaction product of a constituent of the material, and a tag; transmission means, capable of transmitting a signal between the multivariate detector and a data acquisition system, capable of converting the signal into raw data; a computational device capable of processing at least part of the raw data using multivariate analysis to create a data set; and an output device capable of displaying, storing, or using the data set.

The following examples will serve to further typify the nature of this invention but should not be construed as a limitation in the scope thereof, which scope is defined solely by the appended claims.

EXAMPLE I

Analysis of Circuit Boards

Several types of electronic components were analyzed by using a commercially available gas sensor array system (e.g. Prometheus system including mass spectrometer and 12 different metal oxide sensors, Alpha-M.O.S, New-Jersey, USA) equipped with a headspace autosampler (HS100, CTC, Switzerland) and an air conditioning unit (ACU500, Alpha-M.O.S, New Jersey, USA). The electronic component specimens were general purpose PC boards (i.e. epoxy glass based circuit boards), semiconductor logic device (e.g. CMOS dual decoder/demultiplexer) and transistors (e.g. NPN silicon). All samples were weighted (e.g. mass of 1 g) and directly disposed into 20 ml glass vials hermetically sealed with septum caps. The vials were loaded onto a tray of the headspace autosampler for which the following parameters were set; 10 minutes of incubation time in oven at 85° C. with 500 rpm agitation speed, 3 ml headspace capture for injection at 2.5 ml/s into the gas sensing analyzer and 2 minutes flushing of the gas syringe with air (e.g. zero air quality). The sensor acquisition time was set at 2 minutes with an acquisition period of 0.5 second while a delay of 10 minutes was set between consecutive injection. The gas flow rate was typically set at 150 ml/min. In practice, the parameters for mass spectrometry analysis were exploiting similar headspace conditions but a larger volume of headspace injection (e.g. 5 ml) was used. Typically, the instrument was used in a scan mode ranging masses from 1 to 200 amu during 120 seconds acquisition time. The preferred quadrupole mass spectrometer is typically calibrated with PFTBA standard (perfluorotributylamine) on masses 50, 69, 100, 131 and 219. The applicants also observed that applying general good analytical practices (i.e. GC/MS) to obtain proper peak shapes and performance targets may require some modifications of the conditions described above.

Some typical curves illustrating the various sensor responses (FIG. 3) reveal their high sensitivity for the chemical volatiles (e.g. organic VOC's) outgassing from the electronic materials. FIG. 4 shows a map discriminating the various electronic components analyzed with the apparatus described into this application. The various clusters are discriminated based on the different headspace profiles of the samples which can contain, for example, different contaminants or outgasses. FIG. 4 exhibits a discrimination index of 97 which is obtained as an output of a principal component analysis. All components (i.e. group#1, CMOS devices; group#2, transistors; group#3 PC circuit boards) can be viewed as three different groups for identification. Such an information can be then used to feed other types of multivariate analysis algorithm (e.g. cluster analysis, partial least square algorithms) to build a calibration model to further process other measurements in view of comparing new data with selected or reference values, for example, used as quality threshold. Such data also indicate that the present invention addresses the manufacturing needs for a fast high-throughput quality monitoring of electronic components. Another advantage of this invention is that all measurements are non destructive and it is compatible with in-situ monitoring of a manufacturing process. It is also obvious to anyone expert in the state-of-art, that one can substitute electronic component for any encapsulating materials, package, silicon, ceramics, electronic assembly in whole or in part, etc. The invention is also applicable for solving the problem of continuous troubleshooting of an operating electronic device for which operational performance can be compared to some selected specifications. For example, microprocessor performances (e.g. CPU) can be monitored by using a sensing system capable to correlate the outgassing profile to a CPU case temperature (e.g. Pentium P200, 45° C., 18 W; Pentium P166$^+$, Cyrix 6x86, 55° C., 23 W) by training the system to recognize a pattern of normal operating conditions versus a change into a fault pattern. Such an application could provide computer manufacturer with a new alarm device to avoid major crashes of hardware components with costly consequences.

I claim:
1. A non-destructive in situ method for directly monitoring an electronic device, comprising the steps of:
measuring at least one outgas or volatile organic compound of a material, a byproduct of the material, a reaction product of a constituent of the material, or a contaminant of a material of the electronic device, by means of a multisensor array comprising at least one solid-state gas sensor;

detecting more than one property of the outgas or volatile organic compound to produce more than one signal;

combining the signals to produce a signal output which can be processed with a multivariate statistical algorithm; and processing the signal output with multivariate analysis to convert the signal output into information representative of a quality of the material.

2. A method according to claim 1 wherein the multivariate analysis comprises processing the signal output with a pattern recognition algorithm.

3. A method according to claim 2 wherein the multivariate analysis uses unsupervised statistical pattern recognition.

4. A method according to claim 2 wherein the multivariate analysis uses supervised statistical pattern recognition.

5. A method according to claim 1 wherein the analysis is at least one member selected from the group consisting of classical least squares (CLS), inverse least squares (ILS), partial least squares (PLS), principal components analysis (PCA), principle components regression (PCR), nonlinear principle components regression (NLPCR), nonlinear partial least squares (NLPLS), deterministic finite-state automata (DFA), Fast Look-up Algorithm for String Homology (FLASH), pattern recognition, and neural networks.

6. A method according to claim 1 wherein the processing step comprises sensory evaluation of the sample materials by human paneling to determine the quality of the material.

7. A method according to claim 1 wherein the step of measuring uses a near-field probe sensor which comprises a coated optical fiber.

8. A method according to claim 1 wherein at least one outgas or volatile organic compound is collected by a static or dynamic headspace technique in the measuring step.

9. A method according to claim 8, wherein heat, electromagnetic radiation electricity, magnetism, or mechanical vibration assists in transferring the at least one outgas or volatile organic compound from the material.

10. A method according to claim 1 wherein at least one member of the group consisting of a semiconductor gas sensing device, a conductive polymer gas sensing device, a surface acoustic wave gas sensing device, a microbar sensing device, a micromechanical probe, a quartz crystal microbalance, and an optical sensor is used in the detecting step.

11. A method according to claim 1 wherein at least a metal oxide semiconductor gas sensing device is used in the detecting step.

12. A method according to claim 1, wherein the electronic device comprises a circuit board or a multichip module.

13. A method according to claim 1, wherein the outgas or volatile organic compound is at least one member of the group consisting of anions, organic acids, organics, and particulates.

14. A method according to claim 12 wherein the circuit board is in a soldering operation.

15. A method according to claim 12 wherein the circuit board uses surface mount technology.

* * * * *